(12) United States Patent
Jahan et al.

(10) Patent No.: US 11,925,622 B2
(45) Date of Patent: Mar. 12, 2024

(54) ROLE OF NOVEL CARBAZOLE LINKED 1, 2, 3- TRIAZOLE ANALOGS IN ALLEVIATING METHYLGLYOXAL-MEDIATED LATE DIABETIC VASCULAR COMPLICATIONS

(71) Applicants: Humera Jahan, Karachi (PK); Mohammad Iqbal Choudhary, Karachi (PK); Nimra Naz Siddiqui, Karachi (PK); Fatima Z. Basha, Karachi (PK); Shazia Iqbal, Karachi (PK)

(72) Inventors: Humera Jahan, Karachi (PK); Mohammad Iqbal Choudhary, Karachi (PK); Nimra Naz Siddiqui, Karachi (PK); Fatima Z. Basha, Karachi (PK); Shazia Iqbal, Karachi (PK)

( * ) Notice: Subject to any disclaimer, the term of this patent is extended or adjusted under 35 U.S.C. 154(b) by 182 days.

(21) Appl. No.: 17/408,006

(22) Filed: Aug. 20, 2021

(65) Prior Publication Data
US 2023/0054099 A1    Feb. 23, 2023

(51) Int. Cl.
| | | |
|---|---|---|
| *A61K 31/4196* | (2006.01) | |
| *A61K 31/403* | (2006.01) | |
| *A61K 31/4439* | (2006.01) | |
| *A61P 9/12* | (2006.01) | |

(52) U.S. Cl.
CPC ........ *A61K 31/4196* (2013.01); *A61K 31/403* (2013.01); *A61K 31/4439* (2013.01); *A61P 9/12* (2018.01)

(58) Field of Classification Search
None
See application file for complete search history.

(56) References Cited

U.S. PATENT DOCUMENTS

2016/0244435 A1* 8/2016 Eckmann ............. A61K 31/433

OTHER PUBLICATIONS

Miyamoto et al., "Expanded therapeutic potential in activity space of next-generation 5-nitroimidazole antimicrobials with broad structural diversity", 2013, Proceedings of the National Academy of Sciences of the United States of America, 110(43), pp. 17564-17569. (doi/10.1073/pnas. 1302664110) (Year: 2013).*
Iqbal et al., "New carbazole linked 1,2,3-triazoles as highly potent non-sugar (alpha)-glucosidase inhibitors", 2017, Bioorganic Chemistry, vol. 74, pp. 72-81. (http://dx.doi.org/10.1016/j.bioorg.2017.07.006) (Year: 2017).*
Iqbal et al., "Synthesis of new bicarbazole-linked triazoles as noncytotoxic reactive oxygen species (ROS) inhibitors", 2019, Synthetic Communications, 49(18), pp. 2330-2341. (https://doi.org/10.1080/00397911.2019.1620281) (Year: 2019).*
Jahan et al., "Suppression of COX-2/PGE2 levels by carbazole-linked triazoles via modulating methylglyoxal-AGEs and glucose-AGEs—induced ROS/NF-KB signaling in monocytes", 2022, Cellular Signalling, 97(110372), pp. 1-13. (https://doi.org/10.1016/j.cellsig.2022.110372) (Year: 2022).*
Shaikh et al., "Carbazole-Linked 1,2,3-Triazoles: In Vitro β-Glucuronidase Inhibitory Potential, Kinetics, and Molecular Docking Studies", 2019, ChemistrySelect, 4(20), pp. 6181-6189. (DOI: 10.1002/slct.201900647) (Year: 2019).*

* cited by examiner

*Primary Examiner* — My-Chau T. Tran (57) ABSTRACT

The present intervention identifies the antiglycating inhibitors from a series of carbazole-linked 1,2,3 triazole derivatives through in vitro MGO-mediated glycating BSA model. Derivatives 12, and 13 established a remarkable antiglycation activity at the receptor level in human monocytes. These compounds were found non-toxic, and possess the potential to halt AGE-RAGE/ROS-mediated NF-kB-dependent COX-2, and its proinflammatory product, PGE2, production in monocytes. Hence, carbazole-linked 1,2,3 triazole derivatives provide treatment modalities to delay or prevent the onset of late diabetic micro- and macro-vascular complications in diabetic patients.

3 Claims, 9 Drawing Sheets

ROLE OF NOVEL CARBAZOLE LINKED 1, 2, 3- TRIAZOLE ANALOGS IN ALLEVIATING METHYLGLYOXAL-MEDIATED LATE DIABETIC VASCULAR COMPLICATIONS

BACKGROUND OF THE INVENTION

Diabetopathies increase the on-set of morbidity and mortality in diabetic patients. The prevalent diseases, such as nephropathy, retinopathy, and neuropathy are caused by microvascular complications, and lead to end-stage renal disease (ESRD), visual disability, and painful neuropathies, respectively. While, macrovascular dysfunction includes various atherosclerosis-associated disorders, for instance, peripheral vascular disease (PVD), coronary artery disease (CAD), and stroke. These dysfunctions are the consequences of metabolic disorders i.e., chronic hyperglycemia, genetic and epigenetic factors, and increase inflammatory mediators. Chronic hyperglycemia is a critical factor in the development of diabetopathies. Several intracellular cascades have been proposed that target hyperglycemia-induced adverse events on vasculature; hexosamine pathway, oxidative stress, polyol pathway flux, diacylglycerol (DAG)-protein kinase C (PKC) pathway, and advanced glycation end products (AGEs) formation [6]. Consequently, promising drug candidates are required to inhibit the intracellular pathways related to hyperglycemia-mediated adverse effects, and increase the endogenous protective biochemicals in diabetic.

AGEs are formed at an accelerated pace in diabetic hyperglycemic milieu, as a result of non-enzymatic glycation of proteins, lipids, and nucleic acids, and alters the structures and functions of these biomolecules. During AGEs formation, also termed as Millard reaction, Schiff base fragmentation results in the formation of highly reactive dicarbonyl intermediates, such as glyoxal (GO) and methylglyoxal (MGO), which accelerate protein glycation than the precursor glycating agents (glucose, fructose, and ribose). This cascade results in enhanced AGEs production. AGEs cause the initiation and progression of vasculitis in diabetics. In blood vessels, AGEs quench e-NOS-mediated nitric oxide (i.e., an endothelium-derived vasodilator), trap plasma proteins, and interact with signaling receptor, RAGE, to dys-regulate cellular activities. Furthermore, they are associated with the oxidation of plasma low-density lipoproteins (LDL), which in turn stimulate oxidized-LDL (Ox-LDL) formation. Besides, AGE-RAGE ligation on endothelial, and vasculature smooth muscle cells or cells of the immune system, such as monocytes/macrophages, play a critical role in the pathogenesis of vascular function impairment, and hence in the development of atherosclerosis (ATH). Particularly, AGEs interaction with the vessel wall components enhance oxidative stress, procoagulant activity, and vascular permeability. AGEs strongly regulate stages of atherogenesis via activating an inflammatory and proliferative mechanism, and hence enhance vascular perturbation in diabetes.

AGEs initiate cellular inflammatory response nexus via activating blood monocyte by RAGE ligation, expressed on cell surface. These activated monocytes deteriorate the intracellular antioxidant defense mechanism, and thereby elevate oxidative stress, which in turn upregulate redox sensitive transcription factors κβ (NF-κβ). This increase in regulation induces several pro-inflammatory genes; tissue factor (TF), ERK 1/2, Ras, vascular cellular adhesion molecule 1 (VCAM1), intercellular adhesion molecule 1 (ICAM-1), RAGE, and cyclooxygenase-2 (COX-2) [17-21]. Among them, COX-2 stimulates pro-inflammatory mediators, prostaglandin E2 (PGE2), and others in atherosclerosis [22-24]. The AGEs-induced elevated levels of COX-2 and PGE2 causes the activation, migration, and adhesion of monocytes to endothelial cells, thereby leading to vascular dysfunction. Besides, the involvement of COX-2 and PGE2 in adherence of monocytes to vascular smooth cells plays an important role in monocytes retention in vascular wall, and hence progression of atheroma formation. The AGE-RAGE ligation triggers major downstream cell signal transduction pathways, including MAPK pathway, that are involved in the activation of NF-κβ, and increased induction of COX-2 in monocytes.

Linton et al highlighted that the alteration in cyclooxygenase (COX) expression leads to progression of atherosclerosis and thrombosis, such as platelet aggregation and the inflammatory effect. Particularly, COX-2 inhibition plausibly declines the progression of atherogenesis via anti-inflammatory response. Glass and coworkers study on LDL receptor-deficient mice model have revealed the contribution of COX-2 and PGE2 as pathogenic factors for atherosclerotic plaque formation. PGE-2 interacts with monocytes via cell surface scavenging receptors to uptake oxidative low-density lipoprotein (LDL) for fatty streak formation, and atheroma formation.

To understand COX-2-implicated complications, number of studies have been conducted that used nonsteroidal anti-inflammatory drugs (NSAID) as therapeutic strategy. Many of these agents, such as rofecoxib, etoricoxib, valdecoxib, etodolac, celecoxib, nimesulide, diclofenac, and indomethacin have shown the regulation of COX-2 inhibition, but their activity was not more than 50%. Besides, various adverse effects are found for its therapeutic use, for instance gastrointestinal tract inflammation (celecoxib), cardiovascular events (etoricoxib, rofecoxib and valdecoxib), hepatotoxicity (nimesulide), depression (indomethacin), acute pancreatitis (etodolac), and reproductive toxicity (diclofenac). Therefore, the identification of new inhibitors of COX-2 to alleviate vascular impairments in diabetics, without producing adverse effect, is much needed.

Moreover, there are many antiglycation inhibitors, such as guanidines, metformin, pyridoxamine, OPB-9195, N-phenacylthiazolium bromide, alagebrium, atorvastatin, and kremezin that prevent the formation of AGEs at different stages of the Millard reaction. Several studies have been conducted using in vitro cellular, and animal models to study the effect of various glycation inhibitors. However, none of the inhibitors has gained much attention during clinical trial due to their severe adverse effects and/or lower efficacy. The prototype of glycation inhibitor, aminoguanidine (AG), was found to decrease the extent of AGEs-mediated diabetic pathogenesis by trapping reactive dicarbonyls, and halting their conversion to AGEs, impeding AGEs-mediated cross-link formation, and ameliorating free radical formation. Despite this the use of aminoguanidine was not approved due to its serious safety concerns, such as gastrointestinal disturbance, liver impairment, and development of antinuclear antibody, pernicious-like anemia, pancreatic- and renal-neoplastic tumors, and vasculitis.

The 9H-carbazole aromatic moiety and triazole skeleton have known to have activities against a wide range of pathologies. The carbazole skeleton is composed of two benzene rings, attached with 5-membered pyrrole ring. It is reported to have anti-bacterial, anti-malarial, and anti-cancer properties, and prevent Alzheimer's disease. Besides, three nitrogen atoms in aromatic azole ring structure, triazole, also exhibit therapeutic effect via its diverse characteristic of non-covalent interactions for ligation with proteins moiety, such as enzymes, and cell surface or intracellular receptors.

Altogether, the promising glycation inhibitors that are effective in inhibiting various stages of the Maillard reaction, including the formation, as well as receptor level interaction, are the focus of current research. The current invention is based on therapeutic potential of carbazole-linked 1, 2, 3-triazole derivatives in inhibiting MGO-AGEs formation, and suppression of the MGO-AGEs-induced COX-2 expression, and its inflammatory product, $PGE_2$, in monocytes in in vitro diabetic environment to delay or prevent the onset of late-diabetic cardiovascular complications.

BRIEF SUMMARY OF THE INVENTION

Chronic hyperglycaemia facilitates AGEs formation, which activates vascular blood monocytes, and leads to vasculitis in diabetes. The AGE-RAGE ligation triggers ROS dependent NF-κβ-mediated cyclooxygenase-2 (COX-2)-prostaglandin E2 (PGE2) inflammatory nexus in human monocytes, and cause vascular complications. The increased COX-2 production in monocytes is accountable for the pathophysiological conditions, such as hypertension, inflammation, pain, colorectal tumorigenesis, etc. The role of carbazole-triazole derivatives in the inhibition of in vitro MGO-AGEs formation, and alleviated AGEs-induced COX-2 production, and its product PGE2, in monocytes has not been studied before. Our data demonstrated for the very first time that carbazole-triazole derivatives 2-16, and precursor carbazole (1) exhibit in vitro antiglycation activity at various stages of the Mallard reaction. Therefore, the present invention identifies the possible role and intracellular mechanism of selected carbazole-linked 1,2,3-triazoles 2-16 in MGO-AGEs-induced vascular inflammation in human monocytes. In the present intervention, we identified active carbazole-triazole compounds by using in vitro MGO-mediated BSA glycation assay. Among all the synthesized carbazole-linked 1,2,3 triazole compounds, compound 12 has exhibited an excellent antiglycation activity. Compounds 7-8, 11, 13, and 15 were found to exhibit a good activity, while compound 2 has shown a weak potential. The rest of the compounds were found to be inactive in MGO-BSA model. Next, all the active compounds, except compound 7, were to be found non-toxic to hepatocytes (Hep-G2 cell line) and monocytes (THP-1 cell line). They were later tested to inhibit MGO-AGEs-induced oxidative stress in THP-1 monocytes by DCHF-DA technique. Compounds 12, and 13 have shown an excellent ROS production inhibition. Additionally, both compounds halted AGE-RAGE ligation mediated NF-κB translocation, and associated COX-2 production, and PGE2 formation in human monocytes tested by techniques such as immunocytochemistry, immunoblotting, and ELIZA, respectively. Besides, our findings revealed that compounds 12, and 13 exhibit potent inhibition of AGEs-induced COX-2 production (2.11, and 1.34 fold, respectively), comparable to standards PDTC (an NF-κB inhibitor) (MGO-AGEs: 1.60 fold), and rutin (MGO-AGEs: 1.65 fold). Whereas, compound 12 exhibited relatively higher inhibition than the standard quercetin (1.31 fold), while compound 13 was found to be as potent as quercetin. Our study established the role of carbazole-linked 1,2,3-triazoles in halting protein glycation, and associated inflammatory cascade to possibly impede several vascular complications in diabetes.

DETAILED DESCRIPTION OF THE INVENTION

The present invention elucidates the potent glycation inhibitors from a series of synthetic carbazole-linked 1,2,3 triazole derivatives to inhibit AGEs formation, and alleviate AGEs activated proinflammatory signaling cascade in human monocytes.

Example 1

Materials

Methylglyoxal (MGO), bovine serum albumin (BSA), standard antiglycation agents (quercetin, and rutin hydrate), and DCFH-DA were purchased from Sigma-Aldrich Chemical Corporation (St. Louis, Missouri, United States). Dimethyl sulfoxide (DMSO) was purchased from Amersco L.L.C (Ohio, United States). 96-Well flat-bottom non-sterile and sterile polystyrene black fluorescence plate was procured from Corning Inc. (New York, USA). Sodium azide was obtained from Merck (Darmstadt, Germany). Spectrofluorimeter, NF-κB ($p^{65}$), COX-2 antibody, and DAPI were obtained from Thermo Fisher Scientific (Waltham, MA, USA). B-Actin (Cloud-Clone Corp., Wuhan, China). Sodium dihydrogen peroxide ($NaH_2PO_4$) and disodium hydrogen phosphate ($Na_2HPO_4$) were purchased from Duskan Pure Chemicals Co Ltd (Gyeoniggi-do, South Korea). While, ECL, and B-actin antibody were obtained from Sangon Biotech (Shanghai, China), and Cloud-Clone Corp (Wuhan, China), respectively. The Nikon 90i microscope (Tokyo, Japan) was used for the imaging of NF-κB (p 65) translocation. The power blotter XL System Invitrogen, Thermo Fisher Scientific (Waltham, MA, USA) was used to transfer the blot. All chemicals were prepared in deionized water under an aseptic environment at 37° C.

Methodology

In vitro antiglycation activity: The MGO-BSA assay was performed as per optimized protocol of Jahan, H. et al with slight modifications [49]. Initially, the antiglycation activity of parent compound carbazole (1), and carbazole-linked 1,2,3 triazoles 2-16 were identified at 1 mM using MGO-BSA model. Compounds that showed antiglycation activity at 1 mM were diluted serially. BSA (10 mg/mL) incubated with MGO (0.1 M) for 24 h at 37° C. using phosphate-azide buffer (0.1 mM), served as a positive control. The wells with BSA only were taken as negative control. Whereas, rutin and quercetin were used as standard antiglycation agents. After 24 h of incubation, the fluorescence of each well was measured by using microplate reader (Varioskan lux, Thermo Fisher Scientific, 319 Scientific, USA) at 355 nm excitation, and 460 nm emission.

The % inhibition of MGO-BSA-mediated by carbazole-triazole derivatives was quantified by using the following formula:

$$\text{\% Inhibition of fluorescence} = \frac{1 - \text{Fluorescence of test compounds}}{\text{Fluorescence of glycated } BSA} \times 100$$

The $IC_{50}$ of active antiglycation compounds were identified by using EZ-FIT Enzyme Kinetics Program (Perrella Scientific Inc., Amherst, USA).

Figure 1:
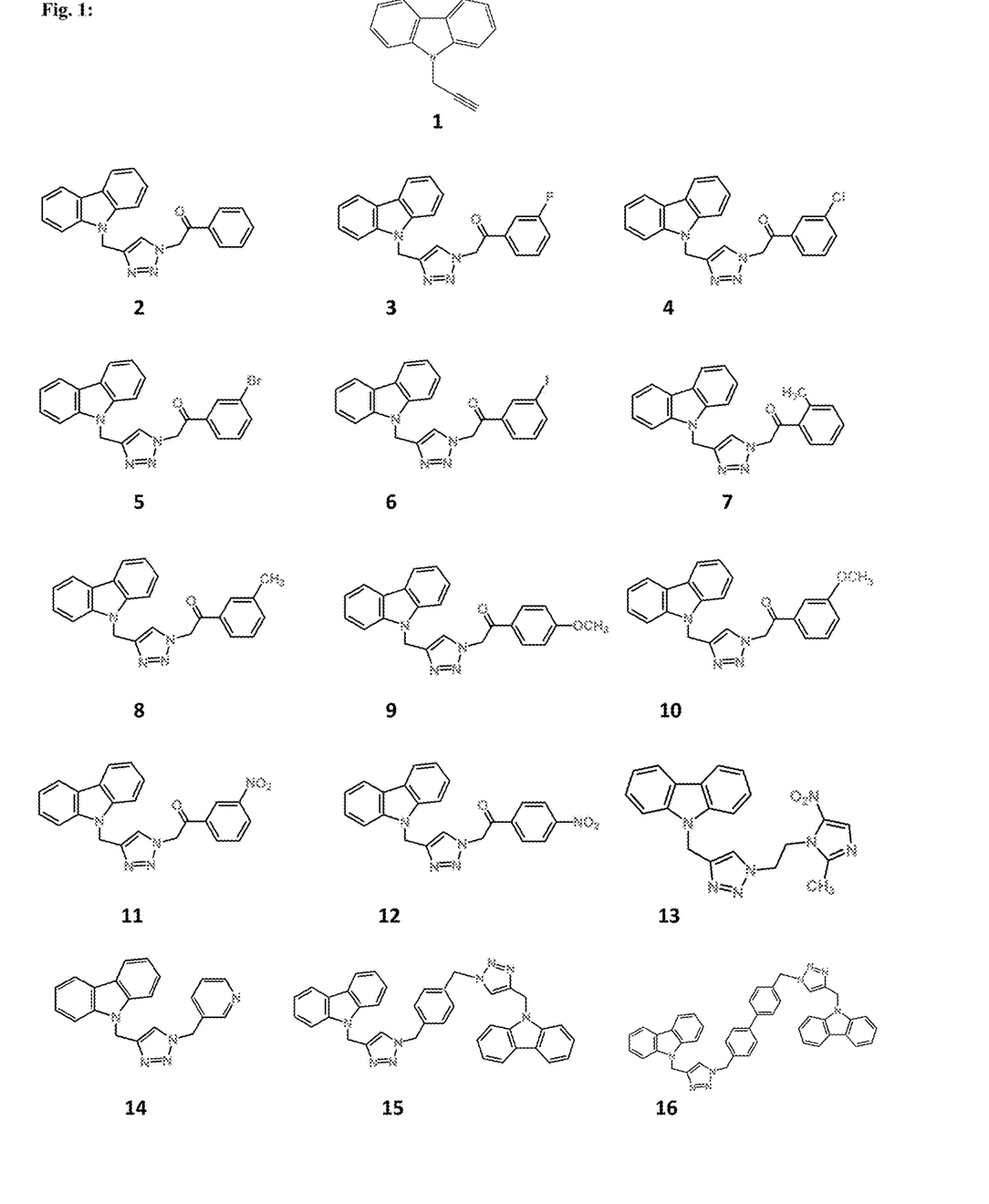
FIG. 1 depicts the chemical structure of carbazole-linked 1,2,3 triazole derivatives 2-16, studied for their antiglycation activity at various levels of the Maillard reaction.
Figure 2:
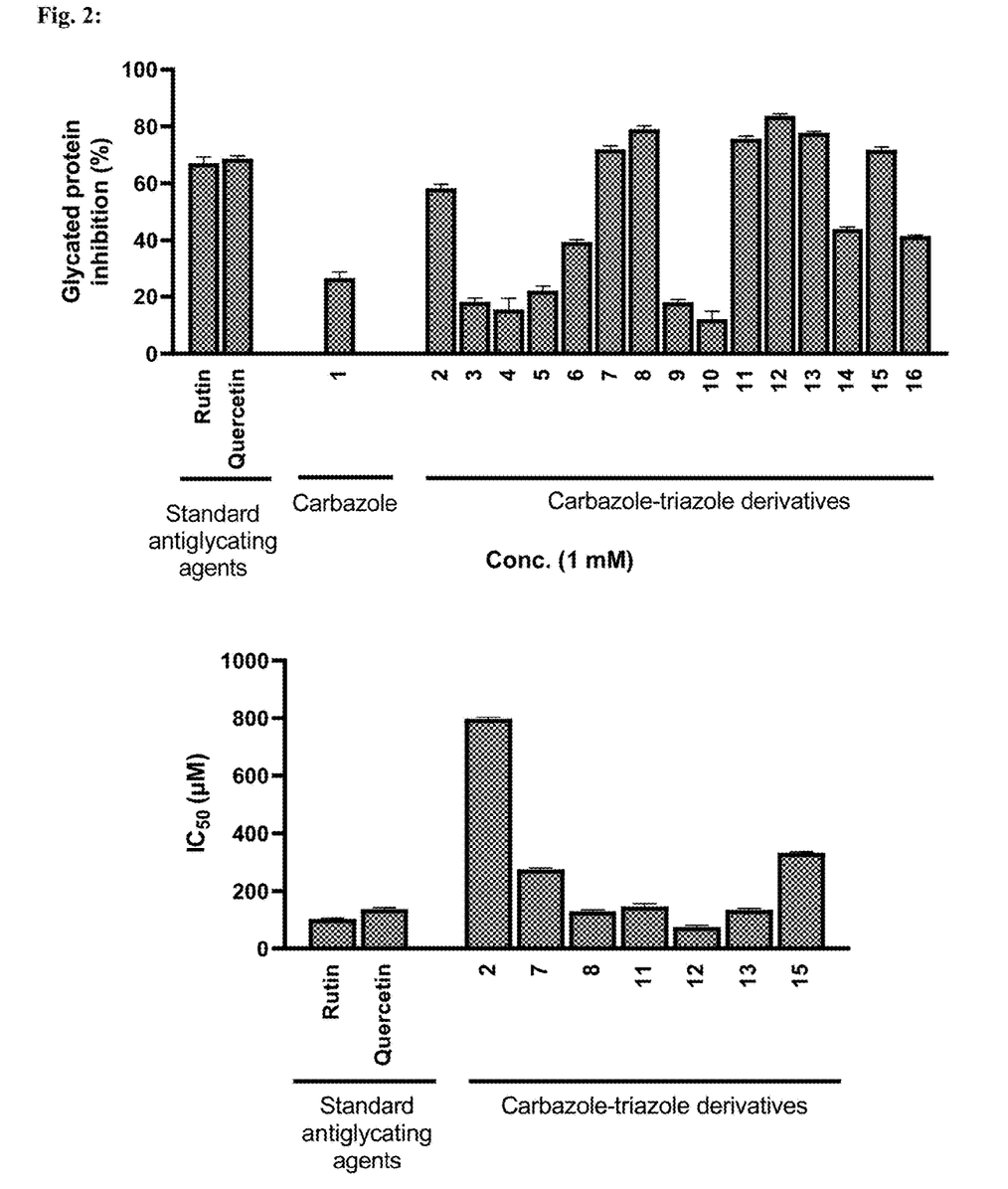
FIG. 2 depicts an illustration of antiglycation activity of derivatives 2-16 in MGO-mediated BSA glycation model.

Results: The antiglycation activity of carbazole-linked 1,2,3 triazoles 2-16 and parent compound carbazole (1) was measured in MGO-BSA glycating model. The structures of carbazole-linked 1,2,3 triazole derivatives 2-16, and carbazole (1) are presented in FIG. 1. All these compounds exhibited greater activity, as compared to precursor carbazole (36.7% inhibition). Among all the compounds, compound 12 (83.7% inhibition, $IC_{50}$: 76.1±6 µM) exhibited an excellent antiglycation activity, as compared to standard compounds, i.e., rutin (67% inhibition, $IC_{50}$:104±2 µM), and quercetin (58% inhibition, $IC_{50}$: 138±4 µM). Compounds 7 (72% inhibition, $IC_{50}$: 275±5.0 µM), 8 (79% inhibition, $IC_{50}$: 130±10.0 µM), 11 (75.7% inhibition, $IC_{50}$: 147±10.004), 13 (77.8% inhibition, $IC_{50}$: 135±5.0 µM), and 15 (71% inhibition, $IC_{50}$: 333±10.004) had shown good antiglycation activity, while compound 2 (58% inhibition, $IC_{50}$: 797±7.0 µM) had exhibited a weak activity. On the other hand, compounds 3-6, 9-10, 14, and 16 (18.2, 15.6, 22, 39, 18,1, 12.1, 43.9, and 41.5% inhibition, respectively) were found to be inactive in MGO-BSA glycation model, as depicted in FIG. 2.

Example 2

Cytotoxicity analysis: The cytotoxic profile of the compounds was determined by using the MTT assay in hepatocytes (HepG2 cell line), and WST-1 assay in human monocytes (THP-1 cell line) as per the manufacturer's protocols. The $20\times10^4$ THP-1/mL, and $7\times10^4$ Hep-G2/mL were plated in sterile 96-well flat bottom plates. The cells were exposed to a series of concentrations (10, 30, 50, 100, 250, and 500 µM) of carbazole-linked triazole derivatives for 24 h. Doxorubicin treated cells were used as a positive control, while cells with culture medium served as negative control. Wells with culture medium served as a blank. Followed by the incubation, 20 µL of MTT were added in each well. Later, 100 µL of DMSO were added into wells containing Hep-G2 cells to dissolve formazan crystals. The absorbance was measured by using 540, and 450 nm, respectively (Varioskanmicroplate reader, Thermo Fisher, 319 Scientific, USA).

Results: The compounds that exhibited antiglycation activity (compounds 2, 7-8 and 11-13 and 15) were selected to quantify their cytotoxicity at different concentrations (10-500 µM) using HepG2, and THP-1 cell lines. The data revealed that compounds 2, 11-13, and 15 were non-toxic till 100 µM, while compounds 7-8, had shown different toxicity profiles, as presented in Table-1.

Viability Assay: The viability of cells treated with various concentrations (10, 30, 100, 200, and 500 µg/mL) of MGO-AGEs was measured by WST-1 metabolic assay. The data revealed that monocytes treated with 50 µg/mL of AGEs were found viable, and hence selected this concentration as a reference to stimulate monocytes for studying the inhibition of intracellular mechanism by potential candidates.

Example 3

Anti-oxidation activity: The measurement of effect of derivatives on AGEs-mediated ROS was based on the previously reported protocol of Soumyarani and colleagues with slight amendments. Initially, $1\times10^6$ monocytes/mL were loaded in sterile 96-well flat bottom black fluorescent plate, and pre-incubated with DCFH-DA (10 µM; Sigma-Aldrich Chemical Corporation, St. Louis, Missouri, USA) for 45 min at 37° C. Followed by the incubation, antiglycating, non-toxic carbazole-linked triazole derivatives (10, 30, 50, and 100 µM) were added to the wells for 1 h before co-treatment of cells with MGO-AGEs (50 µg/mL) for next 24 h. Next, the fluorometric measurement of converted DCFH into oxidized DCF product was carried out via spectrofluorimeter (Varioskanmicroplate reader, Thermo Fisher Scientific, USA) using 485 nm excitation and 520 nm emission wavelengths. Various controls were plated in each experiment. Wells containing culture RPMI with MGO-AGEs (50 µg/mL) and $H_2O_2$ (1011M) served as positive controls, while cells containing BSA were taken as negative control.

Figure 3:
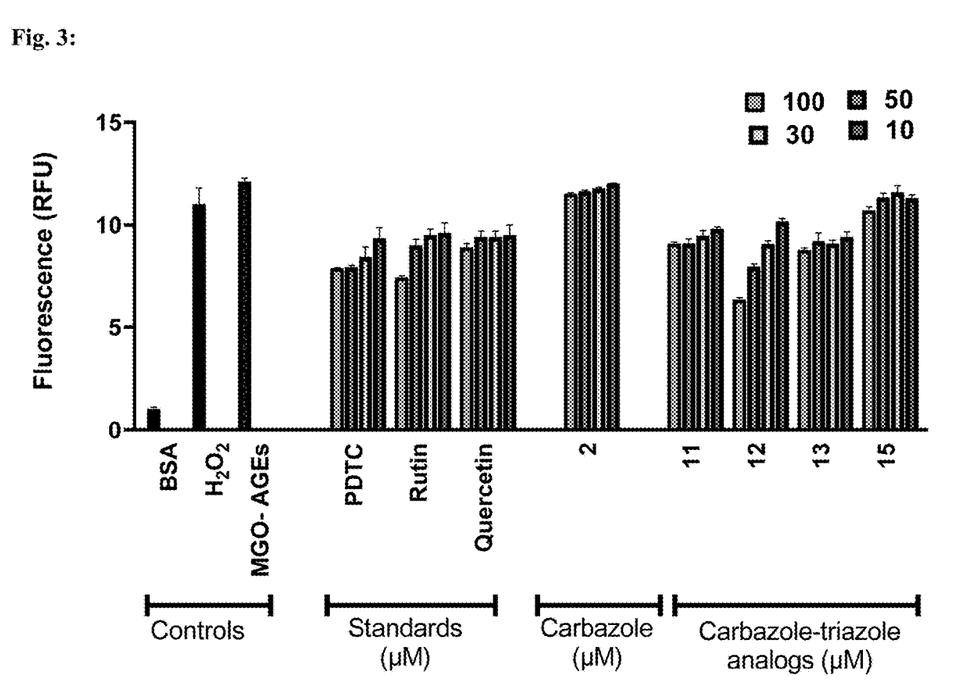
FIG. 3 depicts the antioxidant activity of lead antiglycation derivatives in human monocyte.

Results: The non-toxic, antiglycating carbazole-linked 1,2,3-triazole derivatives 2, 11-13 and 15 were used to identify its anti-oxidative activity against MGO-BSA treated human monocytes. The data revealed that 50 µg/mL of MGO-BSA-treated monocytes exhibit significantly increased ROS formation than the control (untreated- and BSA-treated monocytes), with P-value<0.05. All the wells treated with selected compounds have shown maximum inhibition at 100 µM. Among all, compounds 12 (6.32 RFU), and 13 (8.75 RFU) had shown an excellent antioxidant activity, comparable to standard, rutin (7.44 RFU). Compounds 11 (9.06 RFU), and 15 (10.6 RFU) had shown a moderate antioxidant activity, as compared to standard compounds rutin, PDTC (7.84 RFU) and quercetin (8.39 RFU). While, compound 2 was found to be inactive, as shown in FIG. 3.

Example 4

NF-κB ($p^{65}$) translocation analysis: The monocytes at the density of $1\times10^6$ cells/mL were pre-incubated with compounds (100 µM) for an h, and then co-incubated with AGEs (50 µg/mL) for another 1 h in a 24-well plate at 37° C. Following treatment, cells were fixed with paraformaldehyde (4% PFA; 10 min), and permeabilized with Triton X-100 (0.2%; 10 min). Next, the cells were rinsed with chilled PBS three times, and incubated with bovine serum albumin (1% BSA; 1 h) to block the non-specific binding sites. Cells were exposed to primary antibody against NF-κB (p 65) (1:300 dilution, Thermo Fisher Scientific, Waltham, MA, USA) for overnight at 4° C. Subsequently followed by washing the cells with chilled PBS three times, secondary antibody (polyclonal fluorescein isothiocyanate (FITC)-conjugated antibody) to rabbit IgG (1:1000 dilution, Abeam, Cambridge, UK) was used.

Nuclei were counterstained by using DAPI (Thermo Fisher Scientific, Waltham, MA, USA). The BSA-treated monocytes (50 µg/mL) had served as a negative control, while AGEs-treated monocytes (50 µg/mL) as positive control. All the images were taken by using Nikon microscope (Nikon, Tokyo, Japan). The quantification of images was carried out via ImageJ (Image processing and analysis in Java-NIH).

Figure 4A:
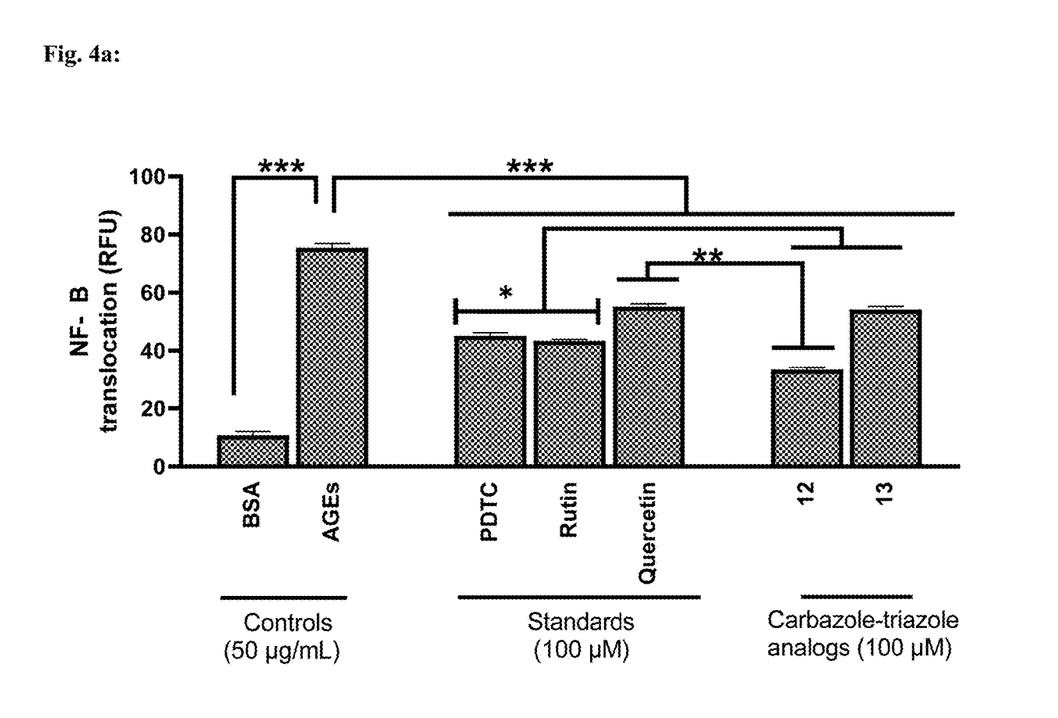
FIGS. 4a and 4b depict the inhibition of AGE-RAGE/ROS mediated NF-kB translocation by selected carbazole-linked 1,2,3 triazole derivatives 12-13 in human monocytes.
Figure 4B:
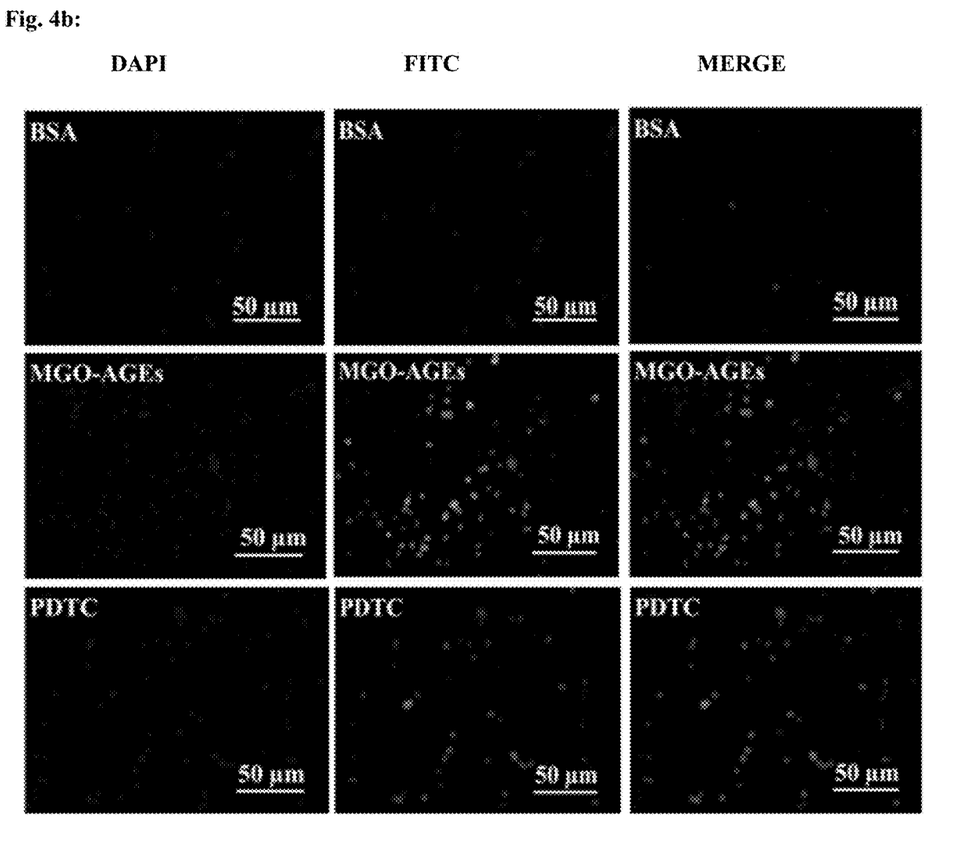

Results: Based on antiglycation, and antioxidant activities, as well as non-toxic profile of compounds 12 and 13, they were selected for the intracellular mechanistic study. Initially, the elevated kB translocation in MGO-BSA-treated human monocytes (MGO-AGEs: 75 RFU) was compared to BSA-treated human monocytes (11 RFU). The pretreatment of monocytes with compounds 12 (33 RFU), and 13 (54 RFU) significantly reduced the NF-κβ translocation by showing P-value<0.05. Both derivatives were found comparatively more effective than standards PDTC (45 RFU), and rutin (43 RFU). While compound 12 exhibited higher activity, and compound 13 exhibited similar level of suppression of NF-κβ translocation than standard quercetin (55 RFU) in MGO-treated human monocytes (FIGS. 4a, and 4b).

Example 5

COX-2 protein levels analysis: The 50 µg/mL of protein was loaded onto 10% sodium dodecyl sulfate-polymerized acrylamide gel electrophoresis (SDS-PAGE), and transferred to nitrocellulose membranes using power blotter XL System (Invitrogen; Thermo Fisher Scientific). Subsequently, the membrane was incubated for 1 h in 1% bovine serum albumin in PBS with 0.1% Tween-20 to block unspecified binding. The protein bands of the membrane were probed with primary monoclonal antibody COX-2 (Thermo Fisher Scientific, Waltham, MA, USA), and B-actin (Cloud-Clone Corp., Wuhan, China) for overnight at 4° C. Following incubation, the membrane was rinsed with tris buffer saline tween (TBST) three times, and then exposed to secondary antibody (HRP mouse mono anti-rabbit IgG; Abeam, Cambridge, UK) at room temperature for an hour. The washing was again carried three times with TBST, and then the membrane was exposed to ECL (Sangon biotech, Shanghai, China) to visualize the bands in Western Blot Detection System (Thermo Fisher Scientific, Waltham, MA, USA). The densitometry of immuno-positive COX-2, and β-actin bands was used by Image J.

Figure 5A:
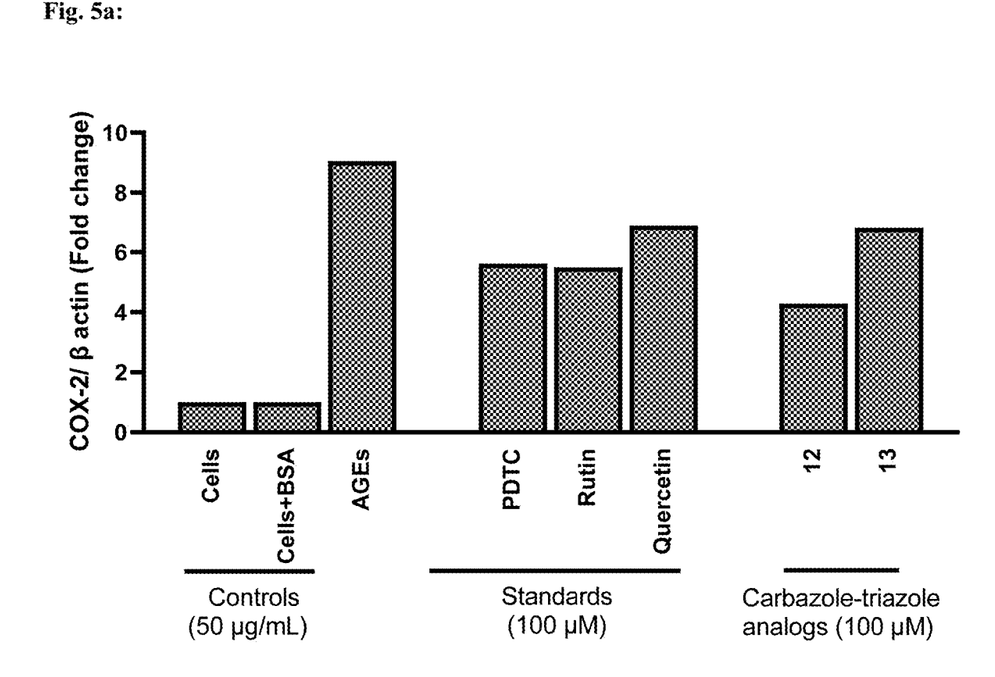
FIGS. 5a, and 5b depict the levels of COX-2 inhibition in human monocytes-cotreated with MGO-AGEs (50 Kg/mL) and carbazole-triazole derivatives 12-13 by employing immunoblotting.
Figure 5B:
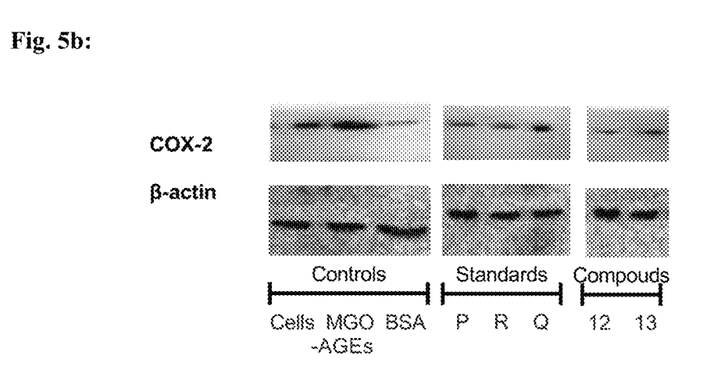

Results: The wells containing MGO-BSA-treated human monocyte models has shown elevated COX-2 enzyme levels, as compared to BSA-treated human monocytes. Followed by the treatment of compounds 12, and 13, a significant reduction in COX-2 levels (3 fold, and 3.5 fold, respectively) was observed, as compared to MGO-BSA-treated cells, by showing P value<0.05, as depicted in FIGS. 5a, and 5b. Furthermore, we found that compounds 12, and 13 were more potent in decreasing COX-2 levels, as compared to standards PDTC (1.60 fold), and rutin (1.65 fold). Whereas, compound 12 exhibited a higher inhibitory effect than quercetin (1.31 fold), and compound 13 showed almost equivalent activity as quercetin.

Example 6

$PGE_2$ levels analysis: ELISA-based method was employed to identify the concentration of $PGE_2$ in culture supernatants of THP-1 cells that was initially exposed with compounds for 1 h, and then stimulated with AGEs (50 µg/mL). All the steps were followed according to the manufacturer's protocols.

Figure 6:
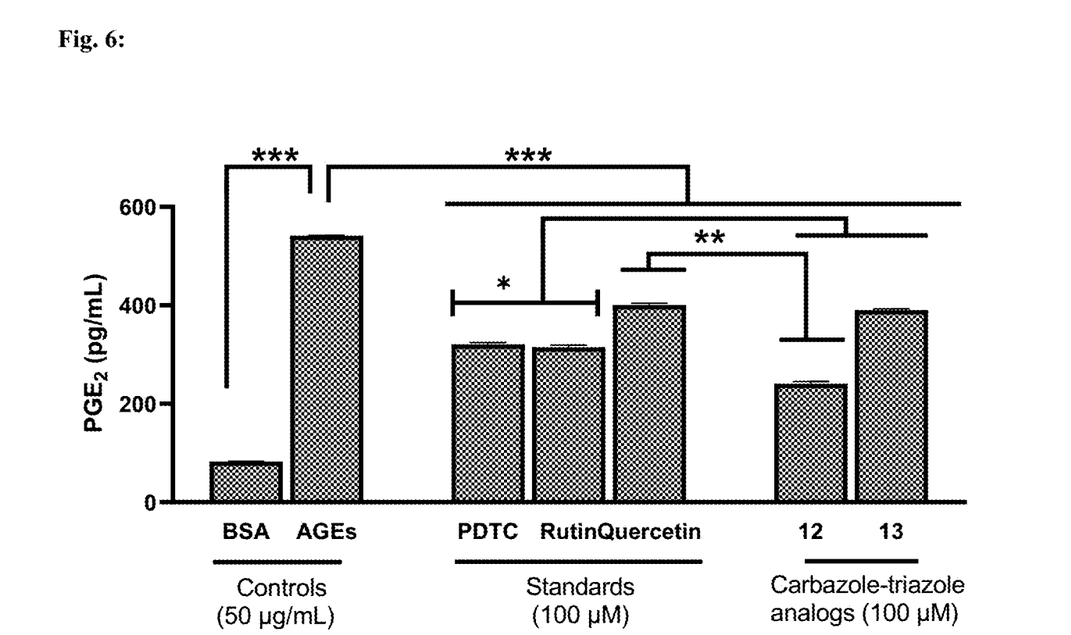
FIG. 6 depicts the inhibition of COX-2 proinflammatory product, PGE2, induced by MGO-mediated BSA glycation via 12-13, representing the potential of compounds to inhibit inflammatory pathway leads to vascular dysfunction.

Results: The data revealed that compounds 12, and 13 reduced $PGE_2$ levels significantly by showing P value<0.05, as compared to control wells (FIG. 6). Consistent with the finding of COX-2 levels, standard PDTC, and rutin exhibited relatively more suppression than quercetin.

TABLE 2

In vitro cytotoxic profile of selected carbazole-triazole derivatives on human monocytes and hepatocytes.

| Compounds | IUPAC | Concentrations (µM) | % Inhibition ± SD | |
|---|---|---|---|---|
| | | | THP-1 | Hep-G2 |
| 2 | 2-(4-((9H-Carbazole-9-yl)methyl)-1H-1,2,3-triazole-1-yl)-1-phenylethan-1-one | 1 | $N_A$ | $N_A$ |
| | | 10 | | |
| | | 30 | | |
| | | 50 | | |
| | | 100 | | |
| | | 250 | | |
| | | 500 | | |
| 7 | 2-(4-((9H-Carbazole-9-yl)methyl)-1H-1,2,3-triazole-1-yl)-1-(o-tolyl)ethan-1-one | 1 | 21 ± 8.8 | 12.3 ± 3.7 |
| | | 10 | 27 ± 4.2 | 21.8 ± 4.7 |
| | | 30 | 34.6 ± 6.5 | 21.8 ± 1.5 |
| | | 50 | 32.1 ± 0.4 | 41.1 ± 3.5 |
| | | 100 | 50.7 ± 5.3 | 50.3 ± 3.9 |
| | | 250 | 80.8 ± 5.1 | 59.8 ± 15.5 |
| | | 500 | 79.5 ± 5.8 | 78.4 ± 2.2 |
| 8 | 2-(4-((9H-Carbazole-9-yl)methyl)-1H-1,2,3-triazole-1-yl)-1-(m-tolyl)ethan-1-one | 1 | 35.5 ± 1.1 | 6.4 ± 2.2 |
| | | 10 | 42.1 ± 0.4 | 8.7 ± 4.8 |
| | | 30 | 43 ± 4.3 | 47.3 ± 2.2 |
| | | 50 | 43.9 ± 0.7 | 54.5 ± 0.7 |
| | | 100 | 46.7 ± 2.0 | 66.9 ± 1.9 |
| | | 250 | 73.6 ± 1.9 | 74.1 ± 1.9 |
| | | 500 | 99.5 ± 0.3 | 86.7 ± 5.8 |
| 11 | 2-(4-((9H-Carbazole-9-yl)methyl)-1H-1,2,3-triazole-1-yl)-1-(3-nitrophenyl)ethan-1-one | 1 | $N_A$ | $N_A$ |
| | | 10 | | |
| | | 30 | | |
| | | 50 | | |
| | | 100 | | |
| | | 250 | | |
| | | 500 | | |
| 12 | 2-(4-((9H-Carbazole-9- | 1 | $N_A$ | $N_A$ |

TABLE 2-continued

In vitro cytotoxic profile of selected carbazole-triazole derivatives on human monocytes and hepatocytes.

| Compounds | IUPAC | Concentrations (μM) | % Inhibition ± SD THP-1 | Hep-G2 |
|---|---|---|---|---|
| | yl)methyl)-1H-1,2,3-triazole-1-yl)-1-(4-nitrophenyl)ethan-1-one | 10<br>30<br>50<br>100<br>250<br>500 | | |
| 13 | 9-((1-(2-(2-Methyl-5-nitro-1H-imidazol-1-yl)ethyl)-1H1,2,3-triazol-4-yl)methyl)-9H-carbazole | 1<br>10<br>30<br>50<br>100<br>250<br>500 | $N_A$ | $N_A$ |
| 15 | 1,4-Bis ((4-((9H-carbazol-9-yl)methyl)-1H-1,2,3-triazol-1yl)methyl) benzene | 1<br>10<br>30<br>50<br>100<br>250<br>500 | $N_A$ | $N_A$ |
| Rutin | 2-(3,4-Dihydroxyphenyl)-5,7-dihydroxy-4-oxo-4H-chromen-3-yl 6-O-(6-deoxy-alpha-L-mannopyranosyl)-beta-D-glucopyranoside | 1<br>10<br>30<br>50<br>100<br>250<br>500 | $N_A$ | $N_A$ |
| Quercetin | 2-(3,4-dihydroxyphenyl)-3,5,7-trihydroxy-4H-chromen-4-one | 1<br>10<br>30<br>50<br>100<br>250<br>500 | $N_A$ | $N_A$ |
| Standard (Doxorubicin) | (7S,9S)-7-[(4S,5S,6S)-4-amino-5-hydroxy-6-methyloxan-2-yl]oxy-6,9,11-trihydroxy-9-(2-hydroxyacetyl)-4-methoxy-8,10-dihydro-7H-tetracene-5,12-dione; hydrochlorid | 1<br>10<br>30<br>50<br>100<br>250<br>500 | 34.2 ± 0.0<br>60.2 ± 0.6<br>63.2 ± 0.4<br>64.5 ± 2.4<br>67.3 ± 0.2<br>76.4 ± 10<br>94.3 ± 2.3 | 30.4 ± 5.3<br>28.3 ± 4.8<br>64.0 ± 0.4<br>58.0 ± 2.4<br>62.6 ± 0.2<br>69.8 ± 10.<br>87.1 ± 2.2 |

S.D. Standard deviation of mean of three independent experiments
$N_A$ = Not active

What is claimed is:

1. A method for reducing the development of diabetes-associated late vascular impairment diabetic atherogenesis progression comprising administration to diabetic patients in need for such treatment, an effective dose of a carbazole-linked 1,2,3-triazole compounds, in a pharmaceutical formulation.

2. The method of claim 1, wherein the carbazole-linked 1,2,3-triazole compounds are 2-(4-((9H-Carbazole-9-yl)methyl)-1H-1,2,3-triazole-1-yl)-1-(4-nitrophenyl)ethan-1-one and 9-((1-(2-(2-Methyl-5-nitro-1H-imidazol-1-yl)ethyl)-1H1,2,3-triazol-4-yl)methyl)-9H-carbazole.

3. The method of claim 1, wherein the diabetes-associated late vascular impairment and diabetic atherogenesis progression comprise AGEs formation, pro-inflammatory biomarkers, COX-2, or associated PGE2 formation.

* * * * *